US012575822B2

(12) United States Patent
Noble et al.

(10) Patent No.: US 12,575,822 B2
(45) Date of Patent: Mar. 17, 2026

(54) METHODS AND INSTRUMENTATION FOR DUROTOMY REPAIRS

(71) Applicant: Arthrex, Inc., Naples, FL (US)

(72) Inventors: Shane Noble, Naples, FL (US); G. Joshua Karnes, Estero, FL (US); Zak Kemp, Naples, FL (US); Peter J. Dreyfuss, Naples, FL (US); Michael A. Gallizzi, Denver, CO (US); Edison P. Valle-Giler, Naples, FL (US)

(73) Assignee: Arthrex, Inc., Naples, FL (US)

( * ) Notice: Subject to any disclaimer, the term of this patent is extended or adjusted under 35 U.S.C. 154(b) by 736 days.

(21) Appl. No.: 17/932,000

(22) Filed: Sep. 14, 2022

(65) Prior Publication Data

US 2024/0081809 A1     Mar. 14, 2024

(51) Int. Cl.
*A61B 17/04*         (2006.01)
*A61B 17/06*         (2006.01)

(52) U.S. Cl.
CPC ..................... *A61B 17/0469* (2013.01); *A61B 2017/0445* (2013.01); *A61B 2017/0472* (2013.01); *A61B 2017/0608* (2013.01)

(58) Field of Classification Search
CPC ........ A61B 17/0469; A61B 2017/0445; A61B 2017/0472; A61B 2017/0608; A61B 2017/06057; A61B 2017/06095
See application file for complete search history.

(56) References Cited

U.S. PATENT DOCUMENTS

| | | | | |
|---|---|---|---|---|
| 2,591,063 | A | * | 4/1952 | Goldberg ......... A61B 17/06166 |
| | | | | 606/231 |
| 5,665,096 | A | | 9/1997 | Yoon |
| 5,810,848 | A | | 9/1998 | Hayhurst |
| 8,469,974 | B2 | * | 6/2013 | Skinlo .............. A61B 17/06004 |
| | | | | 606/139 |
| 8,939,999 | B2 | | 1/2015 | Sterrett et al. |
| 9,398,906 | B2 | | 7/2016 | Stone et al. |
| 9,826,972 | B2 | | 11/2017 | Ranucci et al. |
| 10,022,121 | B2 | | 7/2018 | Bouduban et al. |
| 10,342,527 | B2 | | 7/2019 | Suzuki et al. |
| 10,548,590 | B2 | | 2/2020 | Harris et al. |
| 10,667,841 | B2 | | 6/2020 | Yue |

(Continued)

FOREIGN PATENT DOCUMENTS

| | | | | |
|---|---|---|---|---|
| WO | WO-2016036035 A1 | * | 3/2016 | ............. A61B 17/04 |
| WO | 2021175729 A1 | | 9/2021 | |

*Primary Examiner* — Tan-Uyen T Ho
*Assistant Examiner* — Osama Nemer
(74) *Attorney, Agent, or Firm* — Cozen O'Connor

(57) ABSTRACT

Surgical constructs, assemblies, kits and methods of tissue fixation are disclosed. A suture passing instrument includes a curved tip integral with a distal end of a shaft, a hand assembly mounted on a proximal end of the shaft, and a flexible strand attached to one or two needles and loaded through a cannulation of the shaft. The curve-shaped tip is adapted to engage dural tissue during repairs of the dura mater. The suture passing instrument can grasp and manipulate dura mater and can allow multiple suture passes through the dura mater without removal of the instrument from the durotomy site. The suture passing instrument is provided with a safety mechanism that prohibits the needle(s) to be fired into nerves, providing a safe, reliable, inexpensive, and speedy repair of a durotomy.

10 Claims, 7 Drawing Sheets

(56) References Cited

U.S. PATENT DOCUMENTS

| | | | |
|---|---|---|---|
| 10,799,231 B2 | 10/2020 | Best et al. | |
| 2008/0077162 A1* | 3/2008 | Domingo | A61B 17/0469 |
| | | | 606/146 |
| 2008/0140091 A1* | 6/2008 | DeDeyne | A61B 17/0469 |
| | | | 606/144 |
| 2009/0062816 A1* | 3/2009 | Weber | A61B 17/0469 |
| | | | 606/144 |
| 2009/0062819 A1* | 3/2009 | Burkhart | A61B 17/0469 |
| | | | 606/148 |
| 2009/0105751 A1* | 4/2009 | Zentgraf | A61B 17/0482 |
| | | | 606/139 |
| 2010/0241142 A1* | 9/2010 | Akyuz | A61B 17/0483 |
| | | | 606/144 |
| 2011/0202074 A1 | 8/2011 | Talmo et al. | |
| 2014/0316443 A1* | 10/2014 | Fanton | A61B 17/0469 |
| | | | 606/145 |
| 2015/0173743 A1* | 6/2015 | Palese | A61B 17/0482 |
| | | | 606/144 |
| 2017/0143331 A1* | 5/2017 | Kurd | A61B 17/0469 |
| 2018/0256160 A1* | 9/2018 | Kurd | A61B 17/0491 |
| 2019/0008506 A1* | 1/2019 | Kurd | A61B 17/06066 |
| 2019/0365364 A1 | 12/2019 | Chin et al. | |
| 2020/0268378 A1* | 8/2020 | Cichocki, Jr. | A61B 17/06066 |
| 2021/0251624 A1* | 8/2021 | Young | A61B 17/06109 |

* cited by examiner

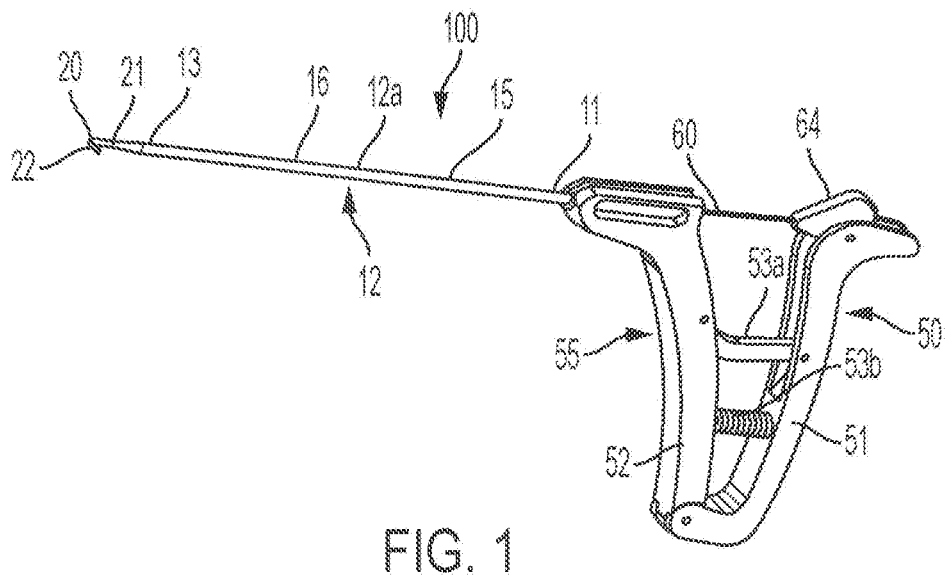
FIG. 1
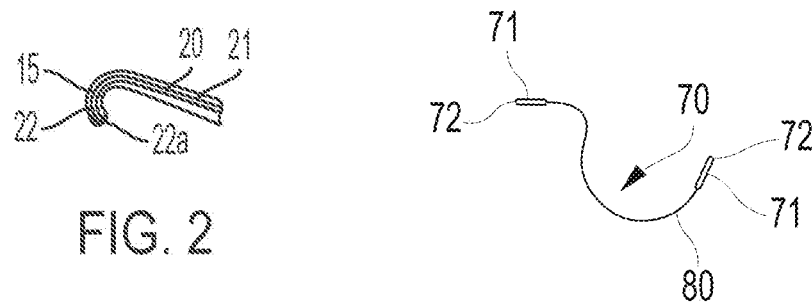
FIG. 2
FIG. 3
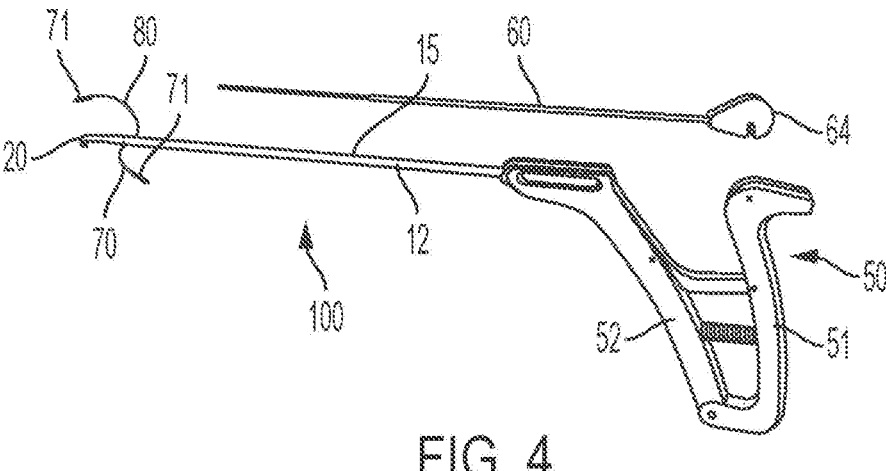
FIG. 4

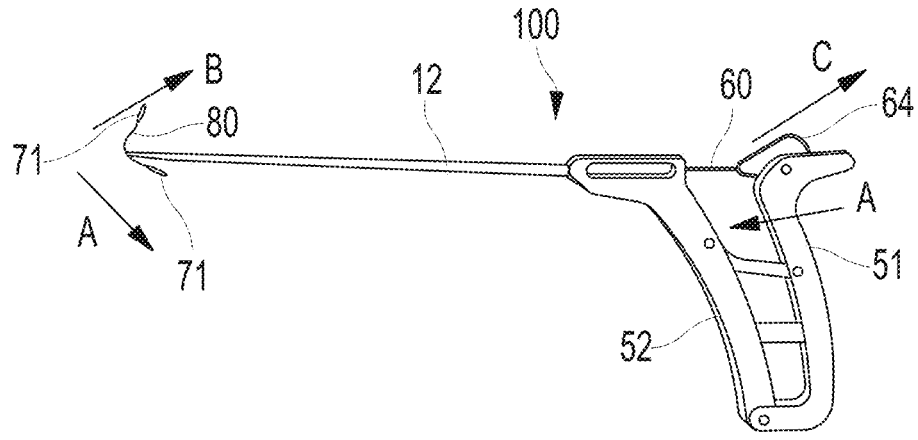
FIG. 5
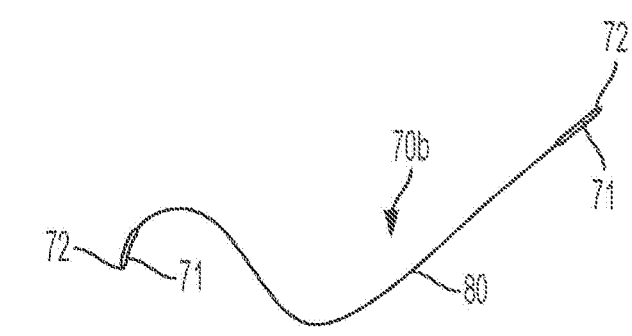
FIG. 6A
FIG. 6B

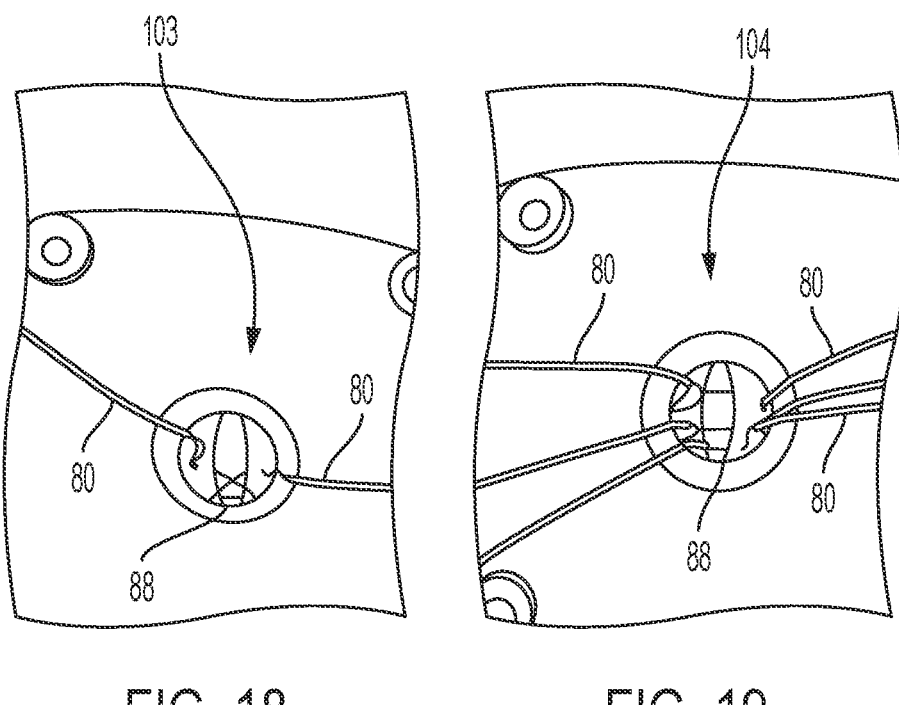
FIG. 18                    FIG. 19
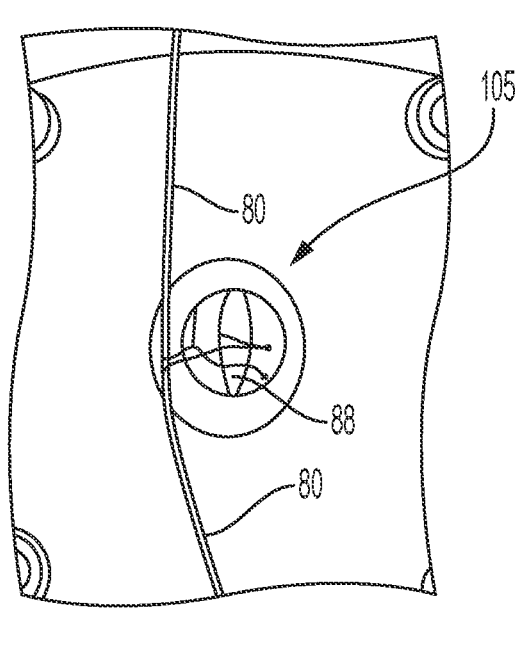
FIG. 20

METHODS AND INSTRUMENTATION FOR DUROTOMY REPAIRS

BACKGROUND

The present disclosure relates to the field of surgery and, more particularly, to suture passing instruments and methods for treating tissue repairs such as durotomies (tears in dura mater).

SUMMARY

Surgical instruments, kits, assemblies and methods for passing suture(s) during dura mater repairs and/or other related procedures are disclosed. A suture passing instrument includes a slotted curved cannula mounted on a distal end of a handle assembly. A suture passing instrument can include a curved tip mounted on a distal end of a shaft, a hand assembly mounted on a proximal end of the shaft, and a flexible needle attached to at least one flexible strand and loaded through a cannulation of the shaft. A flexible needle can be a double ended suture needle. A curve-shaped tip is adapted to engage dural tissue during repairs of the dura mater. A suture passing instrument can include a flexible plunger to allow passing of the flexible needle and of the at least one flexible strand through the curved tip. A hand assembly can move the flexible needle from a first position to a second position.

A suture passing instrument can manipulate dura mater and can allow multiple suture passes through the dura mater without removal of the instrument from the surgical site. A suture passing instrument includes a safety mechanism that prohibits the needle to be fired into nerves, providing a safe, reliable, inexpensive, and speedy repair of a durotomy.

Methods of surgeries are also disclosed. A method of repair of a dura mater defect (for example, a durotomy) includes the step of engaging dura mater to be repaired (sutured) using a suture passing instrument having a curved distal tip and a slotted shaft. The method can include (i) passing a flexible needle and at least one flexible strand attached to the flexible needle through a curved tip of the instrument; and (ii) passing the flexible needle and at least one flexible strand through the dura mater, to close the defect and to repair the durotomy. The method can include passing the flexible needle through a most distal opening of the curved tip and deploying the flexible needle back in a direction away from the dura mater defect, i.e., in a direction back to a surgeon conducting the repair (inside out), to prevent the flexible needle being deployed in a direction toward spinal nerves. The method can include removing the at least one flexible strand through a slot of the shaft; and repeating the steps (i) and (ii) with same or another needle. The method can include conducting multiple suture passes through the dura mater with the same suture passing instrument, and without removing the instrument from the site of the defect. The method can include maintaining the suture passing instrument at the defect site (within the dural sac) for the entirety of the repair, without the need to remove the suture passer after each suture needle pass.

BRIEF DESCRIPTION OF THE DRAWINGS

FIG. 1 illustrates an exemplary surgical instrument.
FIG. 2 illustrates an enlarged view of the curved tip of the surgical instrument of FIG. 1.

FIG. 3 illustrates an enlarged view of a flexible needle and flexible strand (flexible needle/flexible strand construct) for use with the surgical instrument of FIG. 1.

FIGS. 4 and 5 illustrate additional views of the surgical instrument of FIG. 1 illustrating the flexible needle/flexible strand construct loaded on the instrument.

FIG. 6a illustrates another flexible needle and flexible strand (flexible needle/flexible strand construct) for use with the surgical instrument of FIG. 1.

FIG. 6b illustrates another flexible needle and flexible strand (flexible needle/flexible strand construct) for use with the surgical instrument of FIG. 1.

FIGS. 14-20 illustrate subsequent steps of another durotomy repair with the surgical instrument of FIG. 1.

DETAILED DESCRIPTION

Figures 7, 8:
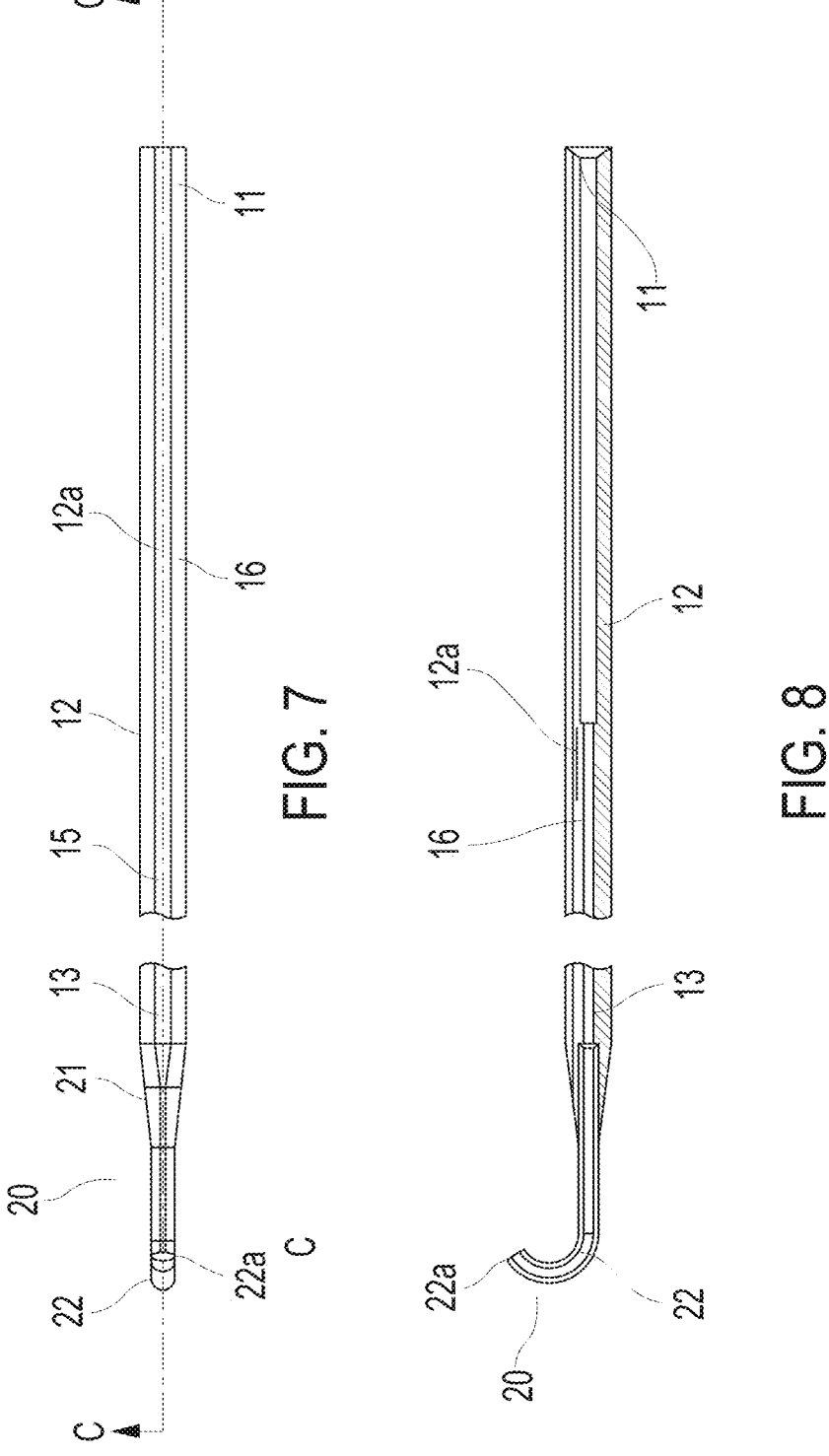
FIG. 7 is a top view of the slotted cannula of the surgical instrument of FIG. 1.
FIG. 8 is a cross-sectional view of the slotted cannula of FIG. 7, taken along line C-C.
Figures 9, 10:
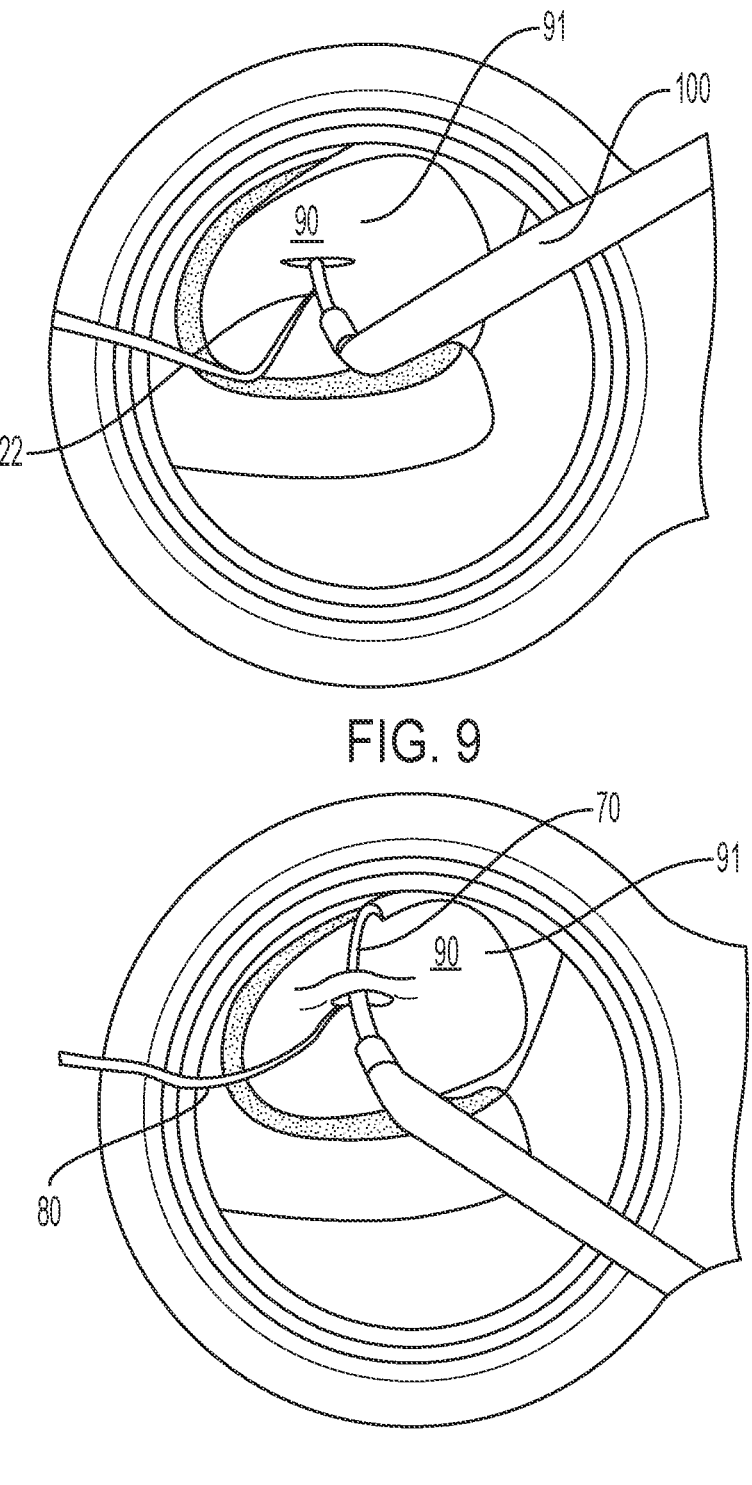
FIGS. 9-11 illustrate subsequent steps of a durotomy repair with the surgical instrument of FIG. 1.

The present disclosure provides surgical instruments, assemblies, kits and methods for correcting and repairing tissue tears such as, for example, spine durotomies (that could be both intentional and incidental).

The present disclosure provides suture passing instruments and techniques for surgical repairs of the dura mater, i.e., repairs of spine durotomies. A suture passing instrument comprises an elongate tubular member and a tip that has a curved configuration and is adapted to be loaded with a flexible, bendable needle and at least one flexible strand (for example, suture) that can be passed through the dura mater to be repaired, and without the need to pull the instrument out of the surgical site to reload flexible strand(s). Multiple passes are conducted by passing at least one flexible strand through the dura mater, without the need to pull the suture passer out of the surgical site to reload the flexible strands (sutures). One or more flexible, bendable needles pass a flexible strand from the instrument through the dura mater at the surgical site.

The elongate tubular member has a slot extending through the entirety of the instrument to allow at least one flexible strand (suture) to be removed from the suture passing instrument in situ, while the instrument is still at the repair site, allowing the instrument to remain in the dural sac for the entirety of the procedure.

Referring now to the drawings, where like elements are designated by like reference numerals, FIGS. 1-8 illustrate exemplary suture passing instrument 100 (instrument 100; device 100; suture passer 100) employed with flexible needle/strand 70, 70a. FIGS. 9-20 illustrate steps of exemplary durotomy repair 101, 102, 103 (repair 101, 102, 103; repair 101, 102, 103 of dura mater tear; repair 101, 102, 103 of dura mater defect) with surgical instrument 100.

As shown in FIGS. 1-5, suture passing instrument 100 comprises an elongate tubular member or shaft 12 having a longitudinal axis 12a, a proximal end 11, a distal end 13 and a longitudinal channel 16 therein. Shaft 12 can be a tube (a needle tube) or a narrow-diameter rod of dimensions that permit the tubular member to be introduced through a larger cannula in a minimally invasive procedure, such as arthroscopic or other endoscopic procedures, or into a body cavity, such as the abdominal cavity. Shaft 12 can be made of steel, steel alloys or similar materials.

Elongate tubular member 12 is provided with a slot 15 (channel 15; aperture 15; opening 15; groove 15) which extends along at least a length of the tubular member 12. Preferably, slot 15 extends throughout the entire length of the tubular member 12, including tip 20, as detailed below. In an embodiment, shaft 12 is an open U channel (i.e., not a closed tube with a continuous outer diameter). In an embodiment, shaft 12 includes a slot with a width that allows at least one flexible strand to pass therethrough, to be removed from the shaft 12.

In an embodiment, shaft 12 includes a longitudinal channel 16 (cannulation 16) and slot 15 provided along the length of the longitudinal channel 16. Slot 15 may be a suture loading slot 15 in communication with the longitudinal channel 16. The longitudinal channel and the slot (loading slot) are configured to allow at least one strand of flexible material (at least one flexible strand) to extend therethrough and to be securely positioned within the shaft 12 and also to be easily removed from the shaft. Slot 15 may have various configurations, for example, a groove (such as a V groove) or a wedge, to allow one or multiple suture positioning for future suture manipulation. The slot 15 is formed integrally with shaft and tip.

Elongated tubular member 12 extends between a handle assembly 50 and a tip 20. Tip 20 is provided at the distal end 13 of the instrument and is preferably integral with the tubular member 12. Tip 20 is provided with a curvature that allows the instrument 100 to provide a secure mechanism for one or more flexible needles to be deployed away from the spinal cord and dura mater defect and towards the surgeon, to prevent damage to the spinal nerves. An enlarged perspective view of tip 20 is shown in FIG. 2. In an embodiment, tip 20 includes a slotted hook. In an embodiment, tip 20 consists of a slotted hook.

In an embodiment, and as illustrated in FIGS. 1 and 2, tip 20 is provided with a substantially straight portion 21 with respect to the shaft, continuing with a curved or substantially curved portion 22 (slotted hook 22; curved hook 22) which communicates with a most distal opening 22a. In an embodiment, portion 22 of tip 20 is curve-shaped, having a certain radius of curvature and provided integral with portion 21 and shaft 12 of the instrument 100. Curve-shaped portion 22 has a diameter smaller than the diameter of the straight portion 21 and smaller than the diameter of the shaft 12. Slot 15 extends throughout the length of the tip 20 and communicates with most distal opening 22a. Additional details of the slotted cannula 12 of the instrument 100 are shown in FIGS. 7 and 8.

Handle assembly 50 of the suturing instrument 100 illustrated in FIG. 1 is provided at the proximal end 11 of the instrument and includes a handle 55 with ends 51, 52 (proximal end 51; distal end 52). The proximal and distal ends 51, 52 of the handle 55 are connected via a link 53a and tension between the proximal and distal ends may be additionally maintained using spring 53b. The link 53a can include a cam and an opening (not shown) so that when the cam is positioned within a first end of the opening, the cam is in a neutral position, and the handles are a maximum distance apart from each other. As the cam moves along the opening (towards a second opening), the handles move towards each other and the cam locks them in a forward position which forces the needle to advance along the longitudinal channel. When the handles are squeezed together and the cam is in the second opening, the cam compresses, traveling to the end of the opening and allows the handles to fully release. This moves a flexible needle 70 through longitudinal channel 16 and out the exit opening 22a. As the needle moves it passes the suture through the dura mater to be repaired.

Exemplary suture passing instrument 100 further includes an actuator 60 which is provided within the shaft 12 and at the distal end of the shaft. FIG. 1 illustrates actuator 60 (flexible plunger 60) provided with thumb pad 64. The slot on the proximal end of the actuator 60 is engaged securely into a cross pin on the proximal end 51 of handle 55 of the suture passing instrument 100. The thumb pad 64 of actuator 60 is pushed down to advance needle/strand 70 construct.

FIGS. 3, 6(a) and 6(b) illustrate exemplary embodiments of flexible needle/strand 70, 70a, 70b (flexible needle/ flexible strand construct 70, 70a, 70b; flexible needle/strand construct 70, 70a, 70b). Flexible needle/strand 70, 70a, 70b is a double ended or single ended suture needle, i.e., a construct with a flexible strand 80 having two opposing ends, each of the two opposing ends terminating in a flexible needle 71 (as illustrated in FIGS. 3 and 6(b)); or a flexible strand 80 terminating on one end in a flexible needle and the other end consisting of the flexible strand 80, as illustrated in FIG. 6(a). Flexible needle/strand 70a, 70b of FIGS. 6(a) and 6(b) are longer needle assemblies to be employed with instrument 100.

The longitudinal channel 16 and tip 20 of instrument 100 are configured to house flexible needle/strand 70, 70a, 70b. When flexible needle/strand 70, 70b is substantially disposed within channel 16, the two needles 71 (and the instrument) are in a non-operative, or non-piercing, position. In an operative position, one of the flexible needles 71 (first needle 71) is advanced distally through the tip 20 to exit most distal opening 22a of hook 22. The needle 71 is bendable and flexible so that it can be moved generally with an axial force and can be bent on a curve, for example, 90 degree to move generally toward the distal opening 22a. Needle 71 can be bent/flexed at any angle and advanced in any direction.

Needle 71 has a pointed tip 72 at a most distal end of the needle and a flexible strand 80 (suture 80). The pointed tip 72 is designed to pierce dura mater 90 (dura 90; dural tissue 90). Preferably, the needle has a generally narrow and elongate configuration with a general straight shape. Needle 71 may preferably be formed of nitinol or other suitable material. Needle 71 can be disposable or reusable. The flexible strand 80 could be crimped, tied, or adhered to the needle 71.

FIG. 4 illustrates instrument 100 loaded with exemplary flexible needle/strand 70, 70b (i.e., the exemplary embodiment with dual needles 71 and at least one flexible strand 80) and with actuator 60 removed from the handle assembly 50.

FIG. 5 illustrates instrument 100 at a durotomy repair step subsequent to that of FIG. 4: (1) load the flexible needle/ strand 70 by inserting one of the two needles 71 (for example, first needle 71) into the channel 16 of the instrument, insert the plunger 60, push the plunger 60 to then fire the first needle 71 (direction of arrow A) so that the first needle 71 and attached flexible strand 80 pass through a first portion of the torn dura mater; (2) remove suture 80 from slot 15 (direction of arrow B); (3) remove flexible plunger 60 (direction of arrow C); (4) insert the other one of the two needles 71 (for example, second needle 71) into the channel 16 of the instrument, insert the plunger 60, push the plunger 60 to then fire the second needle 71 (direction of arrow A) so that the second needle 71 and attached flexible strand 80 pass through a second portion of the torn dura mater; (5) remove suture 80 from slot 15 (direction of arrow B); (6)

remove flexible plunger 60 (direction of arrow C); and (7) repeat the above steps for loading and passing first needle 71 and suture 80 through a third portion of the torn dura mater, and for loading and passing second needle 71 and suture 80 through a fourth portion of the torn dura mater, etc.

As detailed below, using pusher 60 (flexible plunger 60), each of the two needles 71 is advanced to carry the flexible strand (suture) through the dura mater to be sutured. Once the first of the two needles 71 has been deployed through the first portion of the torn dura, the first needle 71 can be retrieved, the plunger removed, and the second of the two needles 71 can be loaded and advanced with the flexible strand through another region of the dura mater (a second region), for additional suture passes.

Although the embodiments above have been illustrated with reference to an instrument having a specific handle configuration, it must be understood that the disclosure is not limited to the above-illustrated embodiment and contemplates additional configurations for the handle assembly and handle. For example, for certain surgical procedures which require locking and/or unlocking, the handle can also include a ratchet-like mechanism that can be pivotally connected to the handle 55. The ratchet-like mechanism can consist of a finger lever with ratchet arms and a releaser, the ratchet arms having a plurality of teeth to engage each other. The finger lever and the ratchet arms perform substantially similarly to a ratchet and a pawl. The finger lever can be pivotally connected by a pivot pin or similar element to the distal end 52 of the handle 55. A releaser can lock and unlock the ratchet arms.

The actuator 60 is designed to move flexible needles 71 from a first position to a second position as the handle ends 51, 52 are brought together, i.e., the handle ends are moved from a first position to a second position. In a first position, needle 71 can be located within the slotted curved cannula of the instrument; in a second position, needle 71 can be located partially outside of the slotted curved cannula, for example, exiting the most distal opening 22 a of tip 20. At the surgical site (the site of the repair of the durotomy), sharp tip 72 of first flexible needle 71 pierces the dura mater 90 to be repaired, at a first piercing location, carrying at least one flexible strand 80 through the dura mater 90 to be repaired. With the instrument 100 maintained at the surgical site, sharp tip 72 of second flexible needle 70 (or another needle) can be reintroduced to allow flexible strand 80 to pass through the dura mater to be repaired, at a location separate from the first location (for example, at a second piercing location). The steps can be repeated again with the first and second needles 71 and flexible strand 80 to form a running stitch or multiple suture passes across the defect. In this manner, the plurality of suture passes can close the dura mater defect in a quick, efficient way, without removing instrument 100 from the surgical site.

The suture passing instrument 100 of the present disclosure, described above with reference to FIGS. 1-8, can be employed in various surgical medical procedures for advancing one or more flexible strands 80 in the proximity of a surgical site, and/or for employing the strand(s) with a cannulated instrument during such surgical procedures, such as repair of durotomy (dura mater tear or dura tear) shown in FIGS. 9-20. Suture passing instrument 100 can be also utilized in other general surgical and specialty procedures that require suturing at a remote site, such as inside the body. The suture passing instrument 100 can be also used in repairs where suture visibility or finger access can be limited and precise handling of a needle or similar sharp instrumentation is obligatory.

Reference is now made to FIGS. 9-13 which illustrate exemplary suturing steps during repair of a dura mater tear (durotomy) and employing the suture passing instrument 100 with exemplary flexible needle/strand construct 70, 70 a, 70 b (single or double-ended suture needle 70). Once suture passing instrument 100 has been loaded with construct 70 with at least one flexible suture strand 80, the suture passing instrument 100 is advanced into the proximity of tissue 90 to be sutured (dura mater 90; dura 90; torn dura 90) at surgical site 91.

With the curved portion 22 of tip 20 around the dura 90, the proximal and distal members 51, 52 of the handle 55 of the handle assembly 50 are squeezed together so that the first needle 71 is advanced distally, exiting the opening 22 a on the tip 22. Once the loaded instrument 100 is gently squeezed with the palm of the hand, the plunger 60 is inserted and the first needle 71 is fired advancing and passing first flexible strand 80 (first suture 80) through the dura 90 at a first location. The method can include retrieving the needle 71 using a retriever or grasper. The steps are repeated to engage and pass second needle 71 attached to flexible strand 80, to pass the flexible strand at a second location through the dura 90 which is different and separate from the first location. The limbs of the passed flexible strand can be secured at the surgical site by, for example, knots 95 (see FIG. 11). Multiple suture passes 88 with flexible strand 80 can be formed to close the dura mater tear without removing the suture passing instrument from the surgical site 91 to complete repair 101 (FIG. 11).

Figures 11, 12, 13:
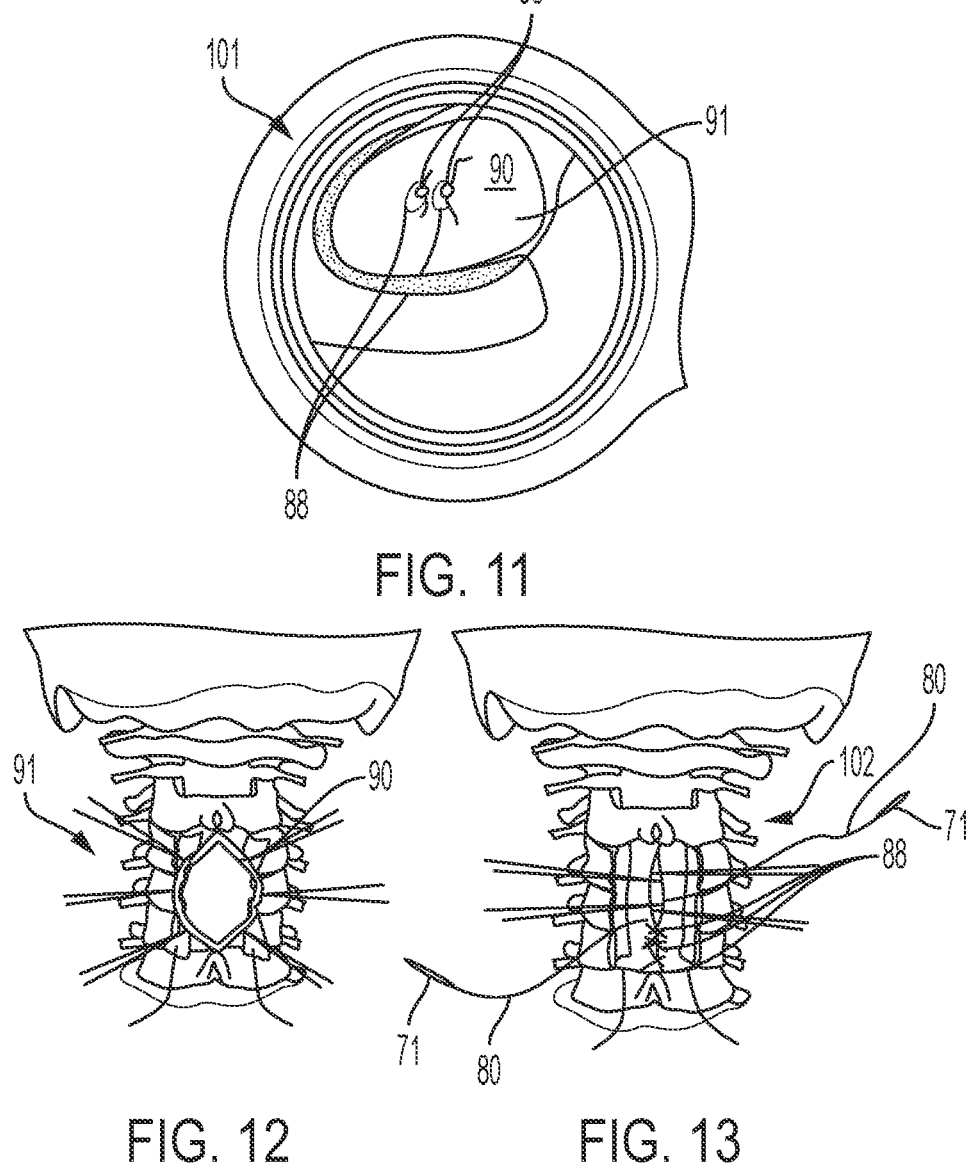
FIGS. 12 and 13 illustrate steps of another durotomy repair with the surgical instrument of FIG. 1.

FIGS. 12 and 13 illustrate exemplary repair 102 (FIG. 13) formed with instrument 100 and double ended suture needle 70, 70 b. Multiple suture passes 88 are provided across the torn regions of dura mater 90 at surgical site 91. The passes form a running stitch by loading and firing the first needle 71 and then the second needle 72 of the double ended suture needle 70, 70 b through opposite ends of the dural tear, in an alternating manner and crossing the suture passes.

Figures 14, 15, 16, 17:
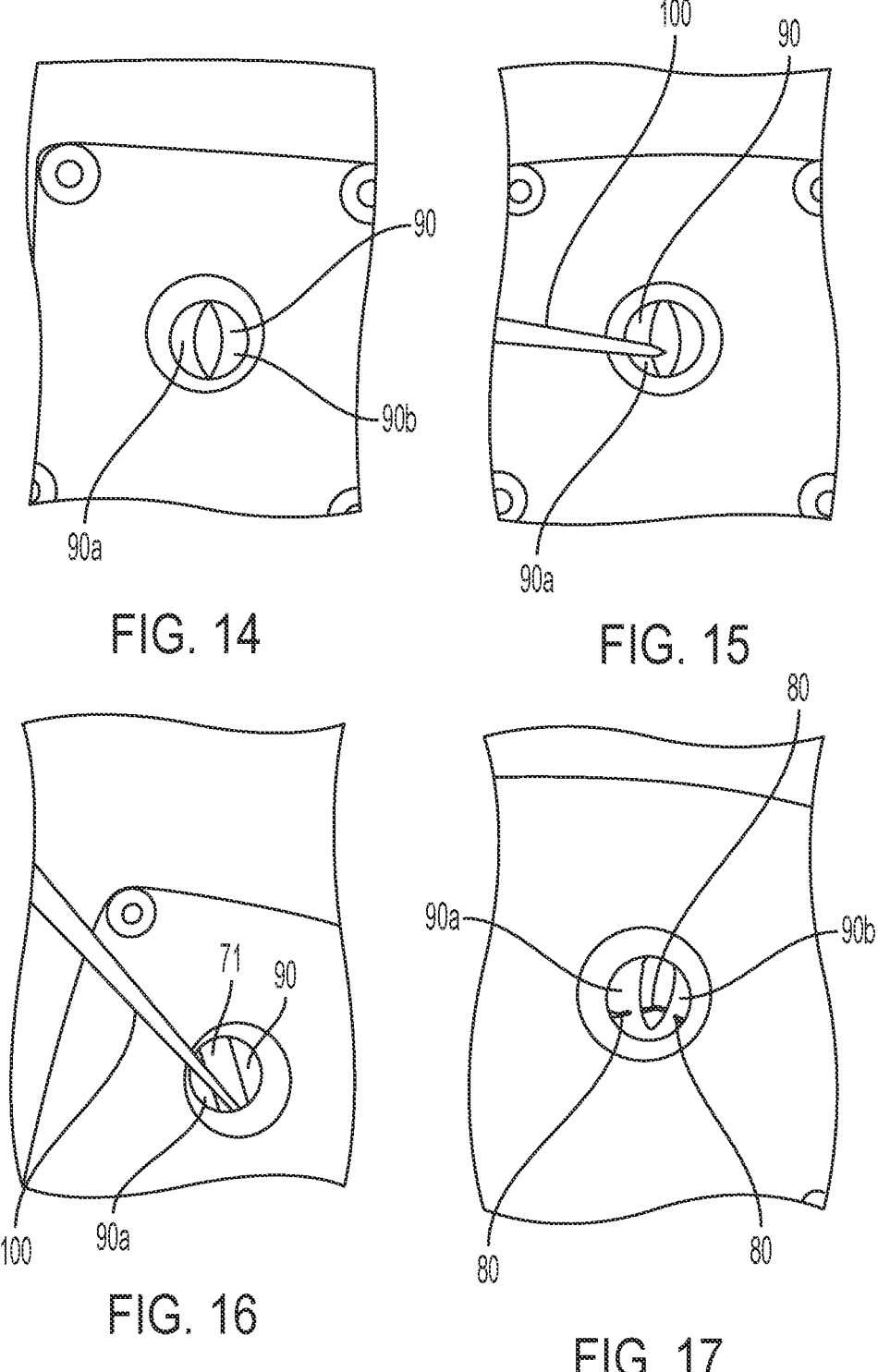

Reference is now made to FIGS. 14-17. Subsequent steps of a dura mater repair with exemplary instrument 100 are set forth below:

1. dura mater 90 appears as pictured in white in FIG. 14;
2. load the first needle 71, insert the plunger 60, and place hook 22 under one side 90 a of tear as pictured in FIG. 15;
3. fire first needle 71 so that it is sticking up through the dura 90 a, as pictured in FIG. 16;
4. remove flexible plunger 60 from mechanism;
5. remove suture 80 through cannula slot 15;
6. repeat steps 2-3 with second needle 71 (the needle on the other end of the suture 80), and fire second needle 71 through the opposite end 90 b of the tear; and
7. dura now appears as pictured in FIG. 17.

Subsequent to steps 1-7 above, methods for completing a durotomy repair can proceed as follows:

FIG. 18 illustrates the formation of a running stitch repair 103. Subsequent to steps 1-7 above, the repair is completed by alternating needles 71, as explained above, and crossing suture 80, as shown above.

FIG. 19 illustrates multiple suture repair 104. After steps 1-7 detailed above, additional sutures 80 are added in the same way (as shown) and tied.

FIG. 20 illustrates the formation of a single needle repair 105. The process is altered to fire and re-fire the same needle (i.e., a single needle 71) multiple times through each side 90 a, 90 b of the tear and finally tied.

In an exemplary and illustrative embodiment only, a method of durotomy repair 101, 102, 103, 104, 105 at a surgical repair site 91 (repair of a dura mater defect 90 or tear 90) using the suture passing instrument 100 of the present disclosure comprises the steps of: (i) passing a flexible needle 71 and at least one flexible strand 80 through anatomical dura 90 to be repaired with suture passing instrument 100; and (ii) conducting one or more suture passes 88 with the flexible needle 71 and/or with another flexible needle 71 through the anatomical dura 90 to be repaired, and without removing the suture passing instrument 100 from the repair site 91.

According to another exemplary and illustrative embodiment only, a method of suturing dura mater 90 and repairing a tear in dura mater with the suture passing instrument 100 of the present disclosure comprises the steps of: (i) positioning a first needle 71 within a slotted curved hook 22 of suture passing instrument 100; (ii) passing the first needle 71 and a flexible strand 80 through anatomical dura 90 to be repaired by actuating actuator 60 of the instrument 100; and (iii) conducting one or more suture passes 88 with the first needle 71 and/or with a second needle 71 through the anatomical dura 90 to be repaired, and without removing the suture passing instrument 100 from the repair site 91. The method further includes the step of deploying the first needle 71 in a direction away from the dura mater defect 90, i.e., in a direction back to a surgeon conducting the repair (inside out), to prevent the first needle 71 from being deployed in a direction toward spinal nerves. The method can include passing the first needle 71 and the flexible strand 80 through a shaft 12 of the instrument 100 and through the curved tip 20; and passing the first needle 71 and the flexible strand 80 through the dura mater 90, and repeating the steps multiple times, to close the defect and to repair the dura mater defect. The method can include passing the first needle 71 through a most distal opening 22a of the curved tip 22 and deploying the first needle 71 in a direction away from spinal nerves. The method can include removing the flexible strand 80 through a slot 15 of the longitudinal channel 16 of the shaft 12 and reloading the instrument with a second needle 71 attached to the flexible strand 80 to conduct at least another suture pass through the dura mater 90. The method can include conducting a plurality of suture passes 88 through the dura mater 90, at different locations in the dura mater, with a same suture passing instrument 100 and without removing the instrument 100 from the site 91 of the defect. The method can include maintaining the suture passing instrument 100 at the defect site 91 (in the dural sac) for the entirety of the repair, without the need to remove the suture passer 100 after each suture needle pass. The method can include retrieving the needle 71 using a retriever or grasper.

A suture passing instrument 100 includes: an elongate body 12 having a distal end 11, a proximal end 13, a cannulation 16, and a slot 15 extending along at least a length of the cannulation; a tip 20 integral to the distal end 13 of the elongate body 12, the tip 20 having a curved configuration, the tip 20 having a most distal opening 22a and a passage; a flexible needle/strand construct 70, 70a, 70b including first and second needles 71 attached to a flexible strand 80, wherein the flexible needle/strand construct 70, 70a, 70b is pre-loaded onto the instrument 100 and passed through the cannulation 16 of the elongate body 12 and through the most distal opening 22a of the tip 20; and a handle assembly 50 provided at the proximal end 11 of the elongate body 12 and configured to move the first and second needles 71, alternatingly, from a first position to a second position and to pass the flexible strand 80 through dura mater 90, wherein each of the first and second needle 71 exits the most distal opening 22a of the tip 20 in a direction away from the dura mater 90 and towards a surgeon conducting repair 101, 102, 103, 104, 105 of the dura mater 90. Slot 15 extends along the whole length of the cannulation 16. Slot 15 extends along the whole length of the tip 20. Slot 15 is configured to release strand 80 from the cannulation 16. The elongate body 12 is a cannula. The handle assembly 50 can include a handle 50 with a proximal end 51 and a distal end 52; and an actuator 60.

A repair system for repair of durotomy includes a suture passing instrument 100; and at least one flexible needle/strand construct 70, 70a, 70b. The repair system can further include additional instrumentation such as graspers and/or retrievers and knot pushers. The suture passing instrument 100 can be disposable. The suture passing instrument 100 can be reloadable. The suture passing instrument 100 can be used in open and endoscopic procedures.

The suture passing instrument 100 can be provided as part of a kit which can include one or more flexible needle/strand constructs 70 (with a flexible strand 80 attached to individual flexible needles 71); flexible strand(s) and needles. The surgical kit can also include a tensioner and associated instrumentation.

By the present disclosure, repair of spine durotomy is achieved with a surgical instrument (such as suture passing instrument 100) that allows more than one suture passes at the repair site without removal of the instrument from the site of the defect.

The device of the present disclosure can be disposable. The device of the present disclosure can be reloadable. The device of the present disclosure can be used in open and endoscopic procedures.

Flexible strand 80 can be high strength suture, tape, suture tape, combination of suture and tape, wire, cable, weave, mesh, ribbon, textile or fabric, or combinations thereof, among many others. Flexible strand 80 can be a round suture or a suture tape, or combination thereof. Flexible strand 80 can be made of any known suture construct, such as multifilament, braided, knitted, woven suture, or including fibers of ultrahigh molecular weight polyethylene (UHMWPE). Flexible strand 80 can consist of, or consist essentially of, suture. Flexible strand 80 can be formed of a high strength suture material such as FiberWire® suture, sold by Arthrex, Inc. of Naples, Fla., and described in U.S. Pat. No. 6,716, 234, the disclosure of which is incorporated by reference herein. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material. Flexible strand 80 can be braided or multi-filament suture such as FiberTape® suture tape (as disclosed in U.S. Pat. No. 7,892,256, the disclosure of which is incorporated in its entirety herewith) or collagen tape, or wide "tape like" material, or combinations thereof.

Flexible strand 80 can consist essentially of suture or suture material, or combination of suture and other materials such as long chain synthetic polymers like polyester and nylon, or materials such as PET, silk nylon or absorbable polymers, or coating materials (such as wax, silk, or silicone products), among many others. Flexible strand 80 can consist of strands with cross-sections of various forms and geometries, including round, oval, rectangular, or flat, among others, or combinations of such forms and geometries. In an embodiment, at least one of flexible strand 80 can be provided as a suture which is braided, knitted or woven. Flexible strand 80 can be absorbable or non-absorbable, or partially absorbable. Flexible strand 80 can be also formed of a stiff material, or combination of stiff and flexible materials, depending on the intended application. Flexible strand 80 can be also coated and/or provided in different colors.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A suture passing instrument comprising:

an elongate body having a distal end, a proximal end, a cannulation, and a slot extending radially through a thickness of the elongate body and open to an exterior surface of the elongate body along a length of the cannulation;

a curved tip integral to the distal end of the elongate body;

a flexible strand attached to one or two needles, the flexible strand being pre-loaded onto the instrument; and a handle assembly provided at the proximal end of the elongate body and configured to move the one or two needles and the attached flexible strand through different regions of a dura mater to be repaired and to conduct one or more passes with the flexible strand, without removing the suture passing instrument from a dura mater repair site.

2. The suture passing instrument of claim 1, wherein the slot is configured to release the flexible strand from the cannulation.

3. The suture passing instrument of claim 1, wherein the elongate body is a cannula or a needle tube.

4. A suture passing instrument comprising:

an elongate body having a distal end, a proximal end, a cannulation, and a slot extending radially through a thickness of the elongate body and open to an exterior surface of the elongate body along a length of the cannulation;

a tip integral to the distal end of the elongate body, the tip having a curved configuration, the tip having a most distal opening and a passage;

a needle/flexible strand construct loaded onto the instrument, the needle/flexible strand construct including a flexible strand with a first end attached to a first needle and a second end attached to a second needle; and a handle assembly provided at the proximal end of the elongate body and configured to alternatingly move the first needle and the flexible strand through a first portion of dura mater, and the second needle and the flexible strand through a second portion of dura mater.

5. The suture passing instrument of claim 4, wherein at least one of the first needle and the second needle is a nitinol needle.

6. The suture passing instrument of claim 4, wherein the slot extends along an entirety of the length of the tip.

7. The suture passing instrument of claim 4, wherein the slot is configured to release the flexible strand from the cannulation.

8. The suture passing instrument of claim 4, wherein the elongate body is a cannula or a needle tube.

9. The suture passing instrument of claim 4, wherein the handle assembly further comprises a handle with a proximal end and a distal end; and an actuator.

10. The suture passing instrument of claim 9, wherein the proximal and distal ends of the handle are linkably connected and tension between the proximal and distal ends of the handle is maintained using springs.

\* \* \* \* \*